(12) United States Patent
Stenger

(10) Patent No.: US 7,385,687 B2
(45) Date of Patent: Jun. 10, 2008

(54) INSPECTION DEVICE

(75) Inventor: Heinrich Stenger, München (DE)

(73) Assignee: Stratus Vision GmbH (DE)

( * ) Notice: Subject to any disclaimer, the term of this patent is extended or adjusted under 35 U.S.C. 154(b) by 396 days.

(21) Appl. No.: 11/041,528

(22) Filed: Jan. 24, 2005

(65) Prior Publication Data

US 2006/0109345 A1    May 25, 2006

(30) Foreign Application Priority Data

Nov. 24, 2004   (DE) ...................... 10 2004 056 698

(51) Int. Cl.
*G01N 21/00* (2006.01)

(52) U.S. Cl. .................... 356/237.1; 348/126; 348/131

(58) Field of Classification Search .. 356/237.1–237.5, 356/394; 348/126, 131; 382/145, 147, 149
See application file for complete search history.

(56) References Cited

U.S. PATENT DOCUMENTS 5,060,065 A  * 10/1991  Wasserman ................. 348/131
5,519,496 A  *  5/1996  Borgert et al. .............. 356/394
6,681,038 B2 *  1/2004  Vilella ........................ 382/145

* cited by examiner

*Primary Examiner*—Hoa Q. Pham
(74) *Attorney, Agent, or Firm*—Robert W. Becker; Robert Becker & Assoc.

(57) ABSTRACT

A device for inspecting a substrate having at least one printed-on layer, including a guide carrier on which the substrate is supported. An inspection head is movable in at least two directions relative to the guide carrier and is provided with an illumination mechanism and an detection device for detecting electromagnetic radiation reflected from the substrate and conveying it to an evaluation device for detecting substrate errors. The detection device has a digital camera with optics for detecting a definition of less than 200 microns. A movement mechanism controls the relative movement between guide carrier and inspection head during an image-taking cycle during which sequential or overlapping individual images can be joined together to form an overall image of the substrate.

20 Claims, 2 Drawing Sheets

INSPECTION DEVICE

This specification for the instant application should be granted the priority date of Nov. 24, 2004, the filing date of the corresponding German patent application 10 2004 056 698.4.

BACKGROUND OF THE INVENTION

The invention relates to an inspection device having an inspection head that is movable in at least two directions relative to a guide carrier that supports a substrate that is to be inspected, whereby the substrate has at least one printed-one layer, whereby the inspection head has an illumination mechanism and a detection device that detects the electromagnetic radiation reflected from the substrate and conveys it to an evaluation device for detecting errors of the substrate.

Such an inspection device is used to test the quality of circuits that in particular are placed or deposited using thick target or layer technology. Such circuits are ordinarily applied in a plurality, for example 20, of layers via screen printing technology. In this connection, it is important that layers containing errors, for example due to mask errors, not be applied.

To check for this, it has become known to test a function of the circuit individually by means of electrical test equipment. The drawback of this is that almost all of the layers have to be applied, and then the testing is undertaken. If the test shows errors, then there is only the possibility of throwing the pertaining chip away, which is accompanied by corresponding cost disadvantages.

It has furthermore also been proposed that optical testing be undertaken during the application of the layers. This can be effected, for example, visually, in other words by a trained operator. However, it has also become known to detect or capture the image of the printed layer or layers via suitable optical detection devices, and to compare the image with a desired image. If the deviation is then too great, the pertaining chip is eliminated.

Numerous approaches have become known in which such inspection devices can be realized and improved. One example is U.S. Pat. No. 4,389,669. With this approach, an optical testing is undertaken using an optical detection device, namely a microscope, accompanied by the use of a camera; in principle, this testing is also suitable for the handling of chips. However, with the customer requirement of a rapid and reliable testing of the electronic circuits or chips, this approach requires a considerable capital outlay for equipment.

A further example for detecting or handling electronic circuits via cameras is disclosed in U.S. Pat. No. 5,245,421, whereby pursuant to U.S. Pat. No. 5,060,065, special illumination devices can also be used to improve the detection possibilities.

Finally, it is known from U.S. Pat. No. 4,673,988 to realize an inspection device using an image that is divided into image areas. This takes place via the image processor that is provided, whereby the object that is to be inspected is movable in two dimensions.

The aforementioned approaches have the common drawback that a relatively great capital expenditure is required, yet an evaluation speed is still to be desired, especially if a plurality of layers of a chip are to be tested. In addition, the precision of detection of the known approaches needs improvement, especially for conceiving an inspection device for a rapid throughput at a low definition, yet where a more precise detection with a specific series of chips is to be undertaken.

It is therefore an object of the invention to provide an inspection device of the aforementioned general type that is further improved with regard to the throughput, and also the precision of detection and the reliability of detection, whereby it should also be possible to have a flexible adaptation to varying requirements.

SUMMARY OF THE INVENTION

This object is realized pursuant to the invention by an inspection device characterized in that the detection device is provided with a digital camera having optics for detecting a definition of less than 200, in particular less than 30, microns on the substrate, and in that the movement mechanism controls the relative movement between guide carrier and inspection head during an image-taking cycle during which sequential or overlapping individual images can be joined together to form an overall image of the substrate.

The inventive approach is characterized by a particularly flexible inspection possibility for chips or the like that is easily adaptable to various requirements yet is reliable. By means of the special illumination mechanism having a plurality of illumination elements, which can, for example, also be grouped in several colors about a tunnel, there is ensured that an intensive illumination is centrally effected at the location that is to be observed by the detection device, and in particular depending upon the type of layer that is applied. In this way, it is not necessary to provide the previously proposed inclined illumination with its drawbacks, and in particular even not when the layers are reflective.

In a modified embodiment, the tunnel is eliminated, and the illumination is ensured by an illumination mechanism that is grouped at a suitable location. In any case, it is particularly advantageous if the image can be strobed, in other words if the illumination of the substrate is effected via the control of the illumination mechanism, while the shutter of the digital camera remains open during the operation.

The reflections are, by the light-emitting diodes that are slightly inclined on all sides and symmetrically convey the light to the detection device, practically diminished in their effect such that the rate of recognition is surprisingly good. It has been surprisingly shown that particularly good results can be achieved in conjunction with the CCD sensor of a digital camera: apparently, the CCD elements that are used in digital cameras are, despite lower definition, more sensitive and hence more selective, which concerns the detection of errors in a scanning field. In a particularly advantageous embodiment of the invention, an error is assumed when three adjacent pixels indicate a value that deviates from the reference image.

It is furthermore particularly advantageous if due to the intensive illumination, which however nonetheless includes a slight, yet not too great inclined positioning, one can also operate at high resolutions with a short illumination time, so that the cycle time for the detection is improved.

In a particularly advantageous inventive embodiment, the detected image is conveyed to a frame grabber that conveys it further to a PC, and only there is the error recognition then effected with a slight time delay.

With this type of pipelining and distribution of tasks, it is possible to achieve a good throughput with a relatively economical technology, so that, for example, it is not necessary to operate the PC in real time.

Typically, for cost reasons a plurality of identical electronic circuits are produced on a common substrate, for example, a wafer or a ceramic substrate. Ceramic substrates can, for example, also have sizes of 20×20 cm. Disposed on such a substrate can, for example, be 50 or even 200 appropriate electronic circuits. Typically, the size (length× width) of a circuit is independent of the taking of the individual image by the inventive digital camera. Pursuant to the invention, there is now provided the possibility of joining together a plurality of individual images by electronic processing in a precise fit to form an overall image, so that the error recognition can be effected considerably more rapidly than if for each testing the digital camera must be precisely focused upon the electronic circuit. The speed is thus in principle independent of the size of the circuits and is merely dependent upon the desired definition and the substrate resolution, which means a considerable advancement over the known approaches.

Pursuant to an advantageous embodiment, the individual images are taken on the fly, in other words, during the relative movement between digital camera and substrate or the guide carrier thereof. This is only possible if the illumination time in relation to the relative movement is short, so that thereby no lack of definitions results. This approach has the advantage that no "after vibration" can trigger a lack of definition during the slowing down of the linear drive, and that the drive is only slightly loaded and hence has a longer life.

This approach entails an intensive illumination in order to obtain a short illumination time.

Pursuant to an alternative embodiment, it is readily possible to stop the movement device for each individual image and to then take the pertaining individual image. As a result, fewer requirements are made of the illumination and the digital camera.

A further particularly advantageous embodiment provides maintaining a basic definition of the digital camera independently of the definition that is to be detected. The adaptation can be realized either by an electronic zoom, or preferably by a true optical zoom in the optics, so that at a greater error tolerance, in other words a lower pixel resolution for the errors, a more rapid cycle time can be achieved.

It is particularly advantageous if the color or the emitted light spectrum of the individual illumination elements can readily be adapted to the particular application. The illumination elements preferably also include UV light-emitting diodes or laser diodes that enable a particularly favorable contrast effect for gold layers. Pursuant to the invention, it is also particularly preferred to adapt the pulse width to the layer materials that are used and to thus undertake an optimization of the error recognition.

It is particularly advantageous if, at a definition of 10 microns or micrometers upon the substrate, the inspection device inspects an individual image of 30×30 mm in less than 10 seconds, especially approximating 4 seconds.

It is to be understood that the inventive tunnel need not necessarily widen conically. A cylindrical tunnel, on the inner periphery of which the illumination elements are secured, in fact makes it possible to operate with even fewer shadows.

In addition, the angle of inclination of the illumination elements that are disposed at a distance from the substrate is greater, which is advantageous in various applications.

BRIEF DESCRIPTION OF THE DRAWINGS

Further advantages, details and features can be derived from the following description of two embodiments of the invention in conjunction with the drawings, in which.

DESCRIPTION OF SPECIFIC EMBODIMENTS

Figure 1:
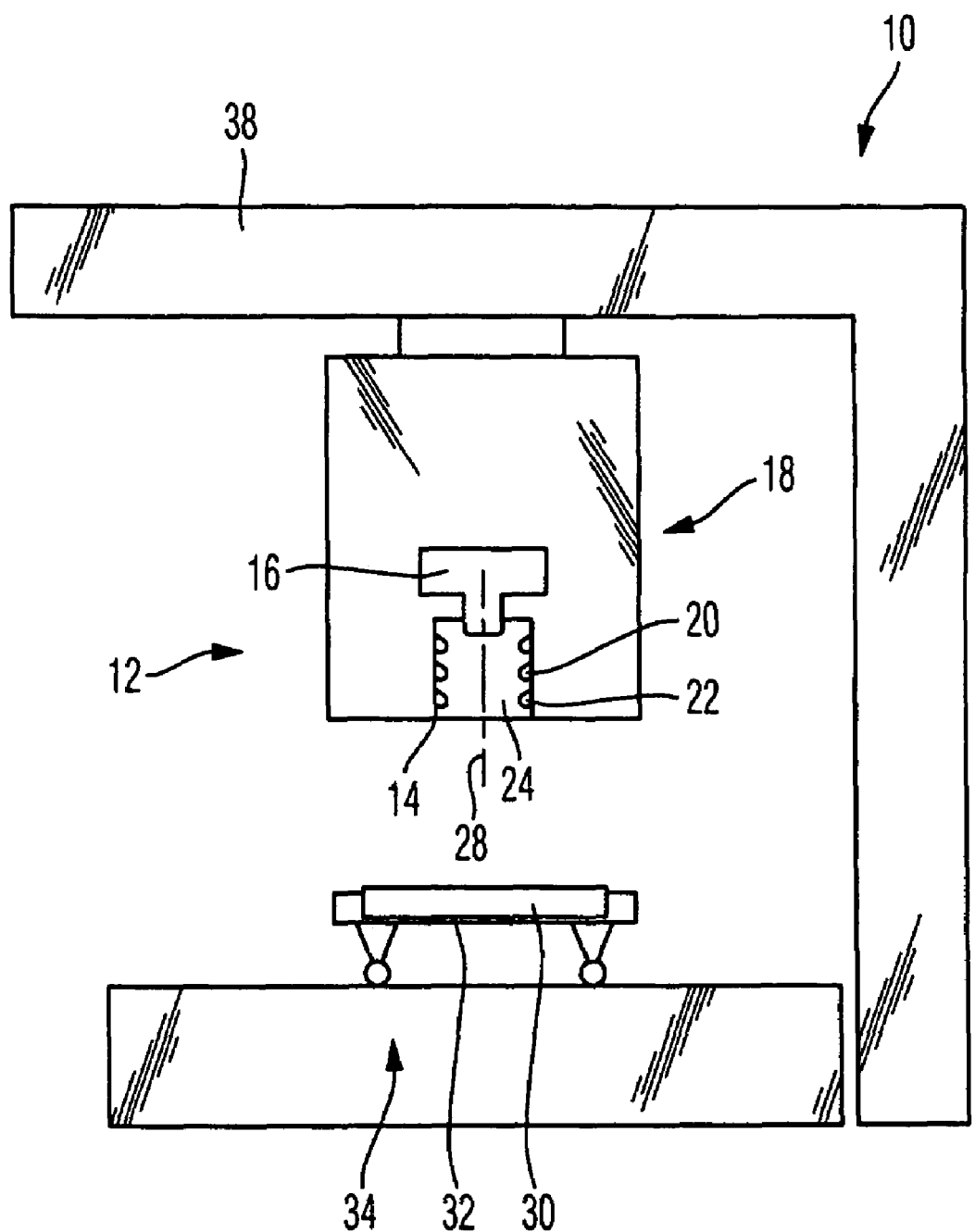
FIG. 1 shows one embodiment of an inventive inspection device.

The inspection device 10 illustrated in FIG. 1 has an inspection head 12 which in turn is provided with an illumination mechanism 14 and a detection device 16.

The detection device 16 has a digital camera 18 and possibly pertaining and not-illustrated optics. The detection device is connected with a non-illustrated evaluation device that processes and evaluates the image data after conversion into electrical signals. For this purpose, a frame grabber as well as a PC are connected, whereby the PC undertakes the adjustable error evaluation.

The illumination mechanism 14 comprises a plurality of light-emitting diodes 20, 22 that are preferably mounted at a slight angle and which are disposed in a tunnel 24. In the illustrated embodiment, the tunnel is cylindrical and the light-emitting diodes 20, 22 are disposed on its inner periphery in different rows or rings. Light-emitting diodes of different colors are used for the various materials that are to be detected.

An optical axis 28 extends centrally through the tunnel 24 and at the bottom encounters a substrate 30. The substrate 30 is mounted on a guide carrier 32. In the illustrated embodiment, the guide carrier 32 is movable perpendicular to the plane of the drawing. Overall, the guide carrier 32 is movable relative to the inspection head 12 in two dimensions via the movement mechanism 34, whereby in the illustrated embodiment, for this purpose the inspection head 12 is movable toward the right and toward the left relative to a frame 38. It is to be understood that the desired ability of the substrate 30 to move relative to the inspection head 12 can be realized in any desirable manner.

The inspection head is now uniformly moved via linear motors or the like of the movement mechanism relative to the substrate 30, and individual pictures or images are taken. The individual images are conveyed to the frame grabber via the digital camera 18 and undertakes the data preparation. In the connected PC, the desired total image is joined together and detected.

It is to be understood that instead of the detection and evaluation of the overall image of the substrate, individual images can also be evaluated with regard to errors, whereby, however, pursuant to the invention the possibility exists of joining the individual images together to form an overall image.

The substrates can be any substrates that are suitable for electronic circuits, for example of ceramic, ceramic fibrit, metal or LTCC. Glass fiber reinforced epoxy resin substrates, or any other suitable substrates, can also be tested.

Figure 2:
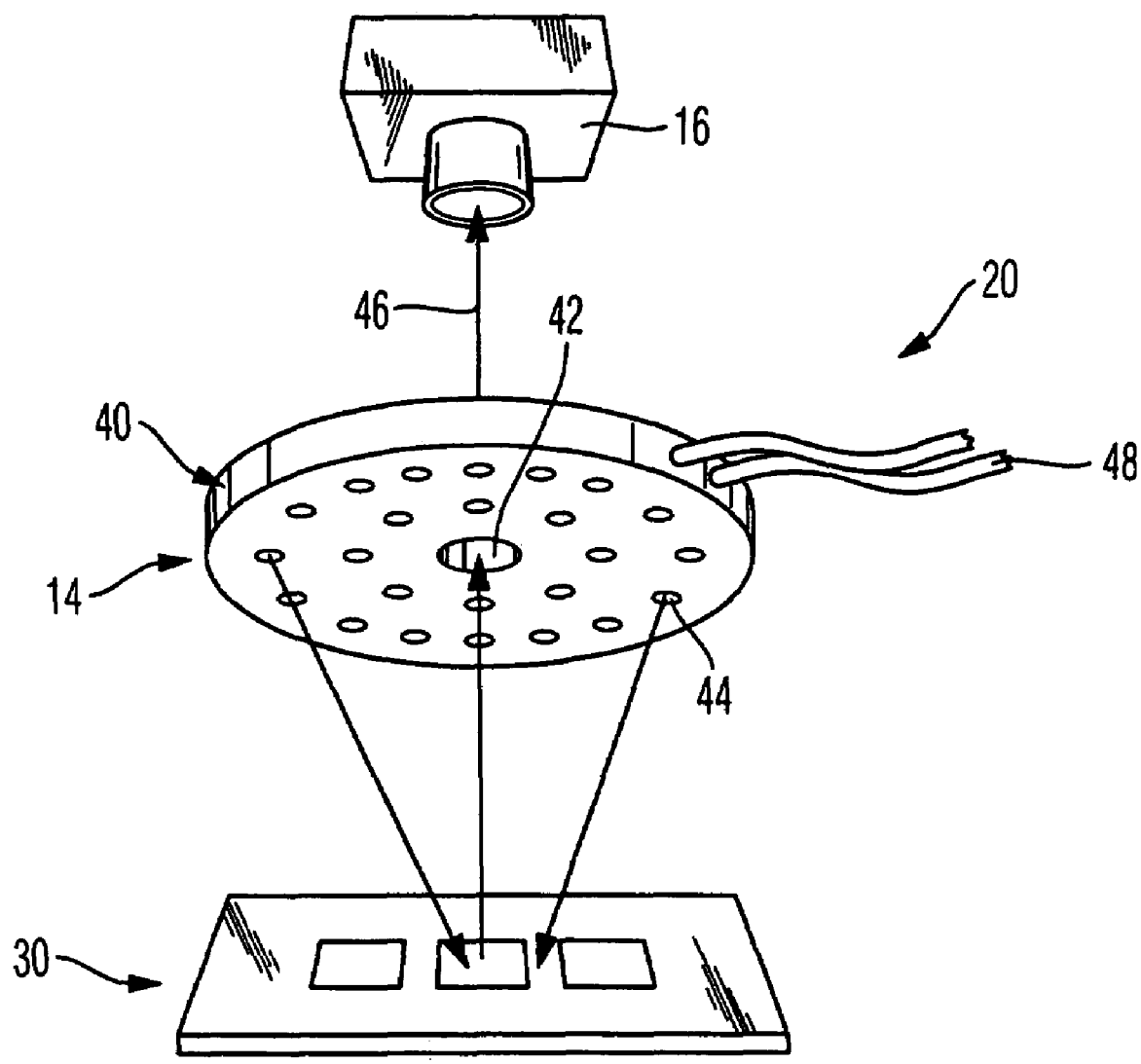
FIG. 2 shows a modified embodiment of a portion of an inventive inspection device.

The inspection device 10 illustrated in FIG. 2 differs from the inspection device of FIG. 1 by a different illumination mechanism 14. In this case, a type of disc 40 is provided that has a central opening 42 and, on its underside, a plurality of light sources or illumination elements 44. The illumination elements 44 provide the desired illumination to the substrate. The reflected light 46 is conveyed to the detection device 16 through the opening 42.

With this approach, the illumination via the illumination elements 44 is effected in a strobed manner, in other words, with the shutter of the digital camera open. Numerous illumination elements 44 can also be provided that, depending upon need, are activated via the cables 48 provided at that location. The cables 48 can be glass fiber cables that convey the light to the illumination elements 44 in a known form, whereby the actual light source can then be disposed at a suitable remote location. Alternatively, the cables 48 can also be electrical connection cables for light-emitting diodes, which are then provided at the locations visible from FIG. 2. It is particularly advantageous that the inspection with the inventive strobe lights, in other words the control of the illumination via the illumination elements 44, can be effected in a single operation or on the fly. This is also particularly advantageous for realizing high definitions.

The specification incorporates by reference the disclosure of German priority document 10 2004 056 698.4 filed Nov. 24, 2004.

The present invention is, of course, in no way restricted to the specific disclosure of the specification and drawings, but also encompasses any modifications within the scope of the appended claims.

The invention claimed is:

1. A device for two-dimensionally inspecting layers of an unassembled substrate that has at least one printed-on layer, said device comprising:
   a guide carrier in which said unassembled substrate that is to be two-dimensionally inspected is disposed;
   an inspection head that is movable in at least two directions relative to said guide carrier, wherein said inspection head is provided with an illumination mechanism and a detection device that is adapted to detect electromagnetic radiation reflected from said unassembled substrate and to convey corresponding signals to an evaluation device for detecting errors of said substrate layer, and wherein said detection device is provided with a digital camera having optics for detecting a definition of less than 200 microns on said unassembled substrate;
   and a movement mechanism for controlling relative movement between said guide carrier and said inspection head during an image-taking cycle during which sequential or overlapping individual images can be joined together to form an overall image of said unassembled substrate.

2. A device according to claim 1, wherein said digital camera has optics for detecting a definition of less than 30 microns.

3. A device according to claim 1, wherein said inspection head has a tunnel that in particular supports illumination elements of said illumination mechanism for illuminating said unassembled substrate.

4. A device according to claim 3, wherein said tunnel is widened at least partially toward said unassembled substrate, in particular in a conical manner, and wherein a plurality of illumination elements of said illumination mechanism are mounted on an inner periphery of said tunnel.

5. A device according claim 1, wherein images can be taken by said digital camera on the fly, and wherein said movement mechanism is controlled so that individual images that sequentially follow or slightly overlap one another can be detected during uniform movement of said movement mechanism.

6. A device according claim 1, wherein an error value that is to be detected can be adjusted by a user of the detection device by adjusting at least one of the optics and an image-taking resolution of said digital camera, and wherein with a more approximate error value, an image size of each individual image can be increased.

7. A device according to claim 1, wherein said illumination mechanism 14 is provided with a trans-illumination unit that is disposed below said guide carrier, optionally moves with said guide carrier, and via which a translucent or transparent substrate can be inspected, and wherein in particular below said guide carrier an LED bed is provided.

8. A device according to claim 1, wherein said unassembled substrate is in the form of at least one of a ceramic substrate, a ceramic fibrit substrate, a metal substrate, an LTCC substrate and a glass fiber reinforced epoxy resin substrate, and wherein said unassembled substrate can be printed-on using multi-layer screen printing technology.

9. A device according to claim 1, wherein said device is part of a production plant for printed-on substrates in which a partially printed on substrate can be fed to the inspection device after printing at least one layer, can then be further printed-on, and can then be again fed cyclically to the inspection device until all layers are inspected.

10. A device according to claim 1, wherein after inspection by the inspection device, each layer can be cyclically introduced into a drying oven or baking oven.

11. A device according to claim 1, wherein to adapt to different materials of said at least one layer, a color of said illumination mechanism can be adjusted, and wherein said illumination mechanism in particular is provided with a plurality of LED's or laser diodes.

12. A device according to claim 1, wherein said illumination mechanism 1 is provided with a light guide or photo conductor, in particular a glass fiber cable, and wherein at least one lens is disposed between said illumination mechanism and said unassembled substrate to increase brightness.

13. A device according to claim 1, wherein said illumination mechanism is provided with a fixed-cycle control via which individual illumination elements of said illumination mechanism can be controlled in a pulsed operation.

14. A device according to claim 1, wherein said illumination mechanism triggers a light pulse to illuminate a pertaining object or target of said digital camera, and wherein said light pulse is synchronized with an image-taking control of said digital camera.

15. A device according to claim 1, wherein said digital camera is provided for detecting an image of said unassembled substrate, wherein a shutter of said digital camera is open, and wherein a digital illumination is effected by controlling said illumination mechanism.

16. A device according to claim 1, wherein illumination elements of said illumination mechanism are disposed in a tunnel that conically widens at an angle 0° to 50°.

17. A device according to claim 16, wherein said tunnel conically widens at an angle of about 20°.

18. A device according to claim 16, wherein said tunnel at least partially faces said unassembled substrate.

19. A device according to claim 1, wherein a frame grabber is connected to said digital camera, and wherein said frame grabber has an output that is connected to a PC that undertakes error recognition.

20. A device according to claim 1, wherein at least two printed-on layers are provided on said unassembled substrate and are in particular applied in an at least partially overlapping and sequential manner.

* * * * *